(12) United States Patent
Sweeney

(10) Patent No.: US 8,337,561 B2
(45) Date of Patent: *Dec. 25, 2012

(54) SPINAL DISC PROSTHESIS SYSTEM

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 331 days.

This patent is subject to a terminal disclaimer.

(21) Appl. No.: 12/722,403

(22) Filed: Mar. 11, 2010

(65) Prior Publication Data

US 2010/0168863 A1 Jul. 1, 2010

Related U.S. Application Data

(62) Division of application No. 10/619,757, filed on Jul. 15, 2003, now Pat. No. 7,695,515.

(51) Int. Cl.
*A61F 2/44* (2006.01)

(52) U.S. Cl. .................................................. 623/17.16

(58) Field of Classification Search ..... 623/17.11–17.16
See application file for complete search history.

(56) References Cited

U.S. PATENT DOCUMENTS

| | | | |
|---|---|---|---|
| 4,309,777 A * | 1/1982 | Patil ........................... | 623/17.13 |
| 4,759,766 A | 7/1988 | Buettner-Janz et al. | |
| 4,863,476 A | 9/1989 | Shepperd | |
| 5,314,477 A | 5/1994 | Marnay | |
| 5,370,697 A | 12/1994 | Baumgartner | |
| 5,545,229 A | 8/1996 | Parsons et al. | |
| 5,562,738 A | 10/1996 | Boyd et al. | |
| 5,645,596 A | 7/1997 | Kim et al. | |
| 5,674,294 A | 10/1997 | Bainville et al. | |
| 5,674,296 A | 10/1997 | Bryan et al. | |
| 5,676,701 A | 10/1997 | Yuan et al. | |
| 5,683,465 A | 11/1997 | Shinn et al. | |
| 5,713,899 A | 2/1998 | Marnay et al. | |
| 5,888,226 A | 3/1999 | Rogozinski | |
| 5,893,889 A | 4/1999 | Harrington | |
| 6,001,130 A | 12/1999 | Bryan et al. | |
| 6,063,121 A | 5/2000 | Xavier et al. | |
| 6,113,637 A | 9/2000 | Gill et al. | |
| 6,139,579 A | 10/2000 | Steffee et al. | |
| 6,146,421 A | 11/2000 | Gordon et al. | |

(Continued)

FOREIGN PATENT DOCUMENTS

DE 3023 353 A1 4/1981

(Continued)

OTHER PUBLICATIONS

ASERNIP-S/RACS: Rapid Review: "Artificial Cervical Disc Replacement," *New and Emerging Techniques—Surgical* (Oct. 2001), 10 pages.

(Continued)

*Primary Examiner* — Pedro Philogene
(74) *Attorney, Agent, or Firm* — Foley & Lardner LLP

(57) ABSTRACT

A disc prosthesis is provided. The disc prosthesis includes a concave surface attached to a first base and a convex surface attached to a second base. The concave surface and the convex surface together form a rotating joint, and at least one of the concave and convex surfaces is attached to its base through at least one flexible support capable of flexing to provide shock absorption when the artificial disc prosthesis is disposed between two vertebra.

9 Claims, 17 Drawing Sheets

U.S. PATENT DOCUMENTS

| | | | |
|---|---|---|---|
| 6,156,067 | A | 12/2000 | Bryan et al. |
| 6,179,874 | B1 | 1/2001 | Cauthen |
| 6,228,118 | B1 | 5/2001 | Gordon |
| 6,368,350 | B1 | 4/2002 | Erickson et al. |
| 6,375,655 | B1 | 4/2002 | Zdeblick et al. |
| 6,375,682 | B1 | 4/2002 | Fleischmann et al. |
| 6,395,034 | B1 | 5/2002 | Suddaby |
| 6,402,785 | B1 | 6/2002 | Zdeblick et al. |
| 6,419,704 | B1 | 7/2002 | Ferree |
| 6,440,168 | B1 | 8/2002 | Cauthen |
| 6,517,580 | B1 | 2/2003 | Ramadan et al. |
| 6,540,785 | B1 | 4/2003 | Gill et al. |
| 6,579,320 | B1 | 6/2003 | Gauchet et al. |
| 6,582,466 | B1 | 6/2003 | Gauchet |
| 6,582,468 | B1 | 6/2003 | Gauchet |
| 6,607,558 | B2 | 8/2003 | Kuras |
| 6,626,943 | B2 | 9/2003 | Eberlein et al. |
| 6,740,117 | B2 * | 5/2004 | Ralph et al. ............... 623/17.14 |
| 6,770,094 | B2 | 8/2004 | Fehling et al. |
| 6,918,934 | B2 | 7/2005 | Ralph et al. |
| 7,105,024 | B2 | 9/2006 | Richelsoph |
| 7,235,102 | B2 * | 6/2007 | Ferree et al. ............... 623/17.12 |
| 7,563,286 | B2 * | 7/2009 | Gerber et al. ............... 623/17.14 |
| 7,695,515 | B2 * | 4/2010 | Sweeney ............... 623/17.14 |
| 2001/0016773 | A1 | 8/2001 | Serhan et al. |
| 2001/0032020 | A1 | 10/2001 | Besselink |
| 2001/0051829 | A1 | 12/2001 | Middleton |
| 2002/0022888 | A1 | 2/2002 | Serhan et al. |
| 2003/0009223 | A1 | 1/2003 | Fehllng et al. |
| 2003/0018390 | A1 | 1/2003 | Husson |
| 2003/0023312 | A1 | 1/2003 | Thalgott |
| 2003/0100951 | A1 | 5/2003 | Serhan et al. |
| 2004/0068318 | A1 | 4/2004 | Coates et al. |
| 2004/0133278 | A1 | 7/2004 | Marino et al. |
| 2004/0243238 | A1 * | 12/2004 | Arnin et al. ............... 623/17.12 |

FOREIGN PATENT DOCUMENTS

| | | | |
|---|---|---|---|
| DE | 3023353 | * | 4/1981 |
| EP | 0 560 140 B1 | | 9/1993 |
| WO | WO 95/26697 A1 | | 10/1995 |

OTHER PUBLICATIONS

Viscogliosi et al., *Spine Arthroplasty: Market Potential & Technology Update* (Muskuloskeletal Research, Nov. 2001), 205 pages.

International Search Report for International Application No. PCT/US04/22826, 3 pages.

Written Opinion for International Application No. PCT/US04/22826, 3 pages.

* cited by examiner

SPINAL DISC PROSTHESIS SYSTEM

CROSS-REFERENCE TO RELATED APPLICATION

This application is a divisional of U.S. application Ser. No. 10/619,757, filed Jul. 15, 2003, which is incorporated herein by reference in its entirety.

FIELD OF THE INVENTION

The present invention relates generally to spinal column intervertebral disc prostheses.

BACKGROUND

It is commonly estimated that about 80% of Americans will see a health care professional at some point in their lives for back problems. Many people claim ongoing back pain as a permanent malady. The majority of these problems are related to the spinal discs. For example, about 250,000 Americans each year undergo surgery for herniated discs.

The spinal column is comprised of 26 interlocking vertebrae. These vertebrae are separated by discs. The spine serves two basic functions: (1) it provides load bearing support for one half of the body's mass and (2) it protects the nerves of the spinal column. The discs serve to provide shock absorption as well as to facilitate the bending of the spine. The discs are formed of a cartilaginous outer structure, the annulus fibrosus, with a gel-like inner structure, and the nucleus pulposus. The nucleus pulposus begins with approximately a 80% water content, but gradually during a person's lifetime the nucleus pulposus loses water and its ability to absorb shock. The disc is susceptible to numerous ailments including, but not limited to, degeneration, bulging, herniation, and thinning, as well as vertebrae related ailments such as osteophyte formation.

Treatment of these ailments has been limited to only a few courses of action. Fusion, or spinal arthrodesis, is a commonly used technique in spine surgery. Clinical studies increasingly suggest that while this surgical technique is likely to result in short-term relief, it does not effectively address the progressive degeneration of the patient's condition in the long run. Fusion restricts the range of motion available to the patient. Further, spinal arthrodesis is associated with premature degeneration of adjacent motion segments, due to the transference of additional stresses and motion from the immobilized segment to the adjacent unfused levels.

Sir John Charnley revolutionized modern orthopedics with the introduction of total hip replacement. Hip and knee arthroplasties are currently two of the most highly rated surgical procedures in terms of patient satisfaction. However, a correspondingly successful and safe method and device for spinal arthroplasties has not been developed.

Artificial disc replacements attempt to accomplish this. The objective of artificial disc replacement is to restore the normal disc height while preserving the natural movement between the vertebrae, thereby alleviating the pain caused by degenerative disc disease. There are two main categories of disc replacement devices: total artificial discs and prosthetic disc nucleus replacements. With respect to the latter, which replace only the soft center of the disc while retaining the firmer disc walls, disc spacer devices can restore normal height, but provide no assurance that a proper seal or structural integrity are achieved.

The average age of a disc replacement patient is under 40, meaning that a disc prosthesis must frequently last 40 or more years. This long product lifetime and the fast pace with which improvements in synthetic discs are being made has created a need for a prosthesis that will provide the surgeon with the ability to easily revise, update, upgrade or replace the disc replacement postoperatively. Additionally, there is a need for surgeons to intraoperatively adjust or modify the prosthesis to compensate for surgical factors. Further, there is a need for an artificial disk prosthesis system that leaves the end plate of the vertebrae adequately exposed such that arthrodesis could be performed postoperatively without removal of the entire prosthesis device. An artificial disc is also needed that can be utilized as a part of a modular artificial disc prosthesis and that provides a degree of shock absorption and flexibility similar to that of a natural disc.

SUMMARY OF THE INVENTION

An artificial disc prosthesis system, a method for revising a disc prosthesis using the artificial disc prosthesis system, and artificial disc prostheses which may be used with the system are provided.

The artificial disc prosthesis system is advantageous in that it allows for postoperative removal and replacement of a stabilizing element, such as a fusion prosthesis or a disc prosthesis without the need to remove the entire prosthesis system. In addition, the artificial disc prosthesis system is capable of being adjusted to accommodate stabilizing elements having different shapes and/or sizes. For example, in some embodiments the artificial disc prosthesis system includes a scaffold assembly that leaves the end plates of the vertebrae to which it is attached adequately exposed such that arthrodesis may be performed subsequent to a spinal disc replacement without removing of the entire artificial disc prosthesis system.

The artificial disc prosthesis system is designed to be inserted into the intervertebral space between two vertebrae and to simulate the motion of a real vertebral disc. The system includes a scaffold assembly. The scaffold assembly, which is attached to at least one of the two vertebrae that define the intervertebral space, is adapted to removably receive a stabilizing member, such as a fusion prosthesis or a disc prosthesis. The scaffold assembly may be composed of a single scaffold unit which is attached to one of the vertebrae between which the scaffold unit is located. Alternatively, the scaffold assembly may be composed of multiple scaffold units which together form a structure adapted to removably receive a stabilizing member. The scaffold assembly is characterized in that it may be adjusted to accommodate stabilizing elements having a variety of shapes and sizes. For example, the scaffold assembly may be adjusted by rearranging or replacing parts of the assembly or by changing the points on the assembly at which the different disc prostheses are attached.

In one embodiment, the scaffold assembly is composed of a superior scaffold unit adapted to be attached to a superior vertebra and an inferior scaffold unit adapted to be attached to an inferior vertebra. In this design one of the scaffold units may have smaller dimensions than the other such that one scaffold unit fits at least partially into the other scaffold unit in a nested configuration when the scaffold assembly is in place between the vertebrae. The scaffold assembly may have a variety of shapes provided it is capable of removably receiving a stabilizing means. The size of the scaffold assembly is desirably tailored to provide, in combination with a disc prosthesis, a normal disc height.

The scaffold assembly includes at least one base which is attached to the end plate of at least one vertebra defining the intervertebral space. In some embodiments the scaffold assembly includes two bases, one attached to each of the vertebrae that define the intervertebral space. The base(s) may be attached to the end plate(s) using conventional means such as fixation pegs, screws, fixation teeth, and the like. In some embodiments, the size and structure of the base(s) are designed to leave enough of the end plates exposed to allow a fusion prosthesis to be inserted between the vertebrae and fused in place without necessitating the removal of the base (s). For example, the base(s) may be substantially ring-shaped such that, in the absence of a disc prosthesis, enough of the end plates are exposed through the center of the ring(s) to allow a fusion prosthesis to be inserted into the intervertebral space and fused in place through the center of the base(s). It should be noted, that the term "ring-shaped" as used herein is not intended to denote only structures having a cylindrical cross-section, instead any structure may be considered ring-shaped provided it has a peripheral section which defines a central opening. Alternatively, the base(s) may be attached to a central portion of an end plate and may be small enough to leave peripheral potions of the end plate exposed. This design permits a disc prosthesis to be removably disposed around and/or over the base(s). Moreover, this design would enable a suitable fusion prosthesis to be disposed around or over the base(s) and fused to the outer portions of the vertebrae without requiring the base(s) to be removed.

In some configurations, the prosthetic disc may be rigidly, but removably, and directly attached to a base of the scaffold assembly at one or more fixation points on the base. Attachment may be achieved using any suitable non-permanent attachment means, including, but not limited to screws, pins, snaps, bands, locking joints, and the like.

In other configurations, the prosthetic disc may be removably retained by the scaffold assembly without being rigidly or directly attached to the base of the scaffold. In one such embodiment, the scaffold assembly includes two bases, each attached to one of the vertebrae that define the intervertebral space. In this configuration, the scaffold assembly further comprises one or more appendages attached to one or both bases. Together with the bases, the appendages define a restricted intervertebral space, or "cage," in which a disc prosthesis may be stably yet removably retained. Using this scaffold design, a stabilizing element could be easily replaced by sliding an old or damaged element out of the cage and sliding a newer or repaired element into the cage without removing the entire scaffold assembly. For example, one or more buttresses may be removably attached to the periphery of one or both bases. The buttresses may extend toward the center of the intervertebral space, such that they define the lateral boundaries of the intervertebral space for a disc prosthesis disposed between the buttresses. The buttresses may be attached to a base using any suitable attachment means, desirably a removable attachment means, including, but not limited to screws, pins, snaps, bands, and the like. The base of the scaffold assembly may be designed such that buttresses may be adjustably attached to the base at different positions and alignments depending on the size and shape of the stabilizing element. This design provides flexibility in the construction of the prosthesis system and allows for disc prostheses having a variety of shapes and sizes to be removably retained by the scaffold assembly. Using this configuration, the disc prosthesis may be inserted into or extracted from the intervertebral space by removing or readjusting one or more of the buttresses on the base to provide an opening into or out of which the disc prosthesis may be inserted or extracted.

In the embodiment described above, the bases of the scaffold assembly may define the top and bottom of the "cage" into which the prosthetic disc is inserted and extracted. Alternatively, the scaffold assembly may further include plates positioned within the intervertebral space above and below the disc prosthesis. The plates may be disposed in a substantially parallel relationship with respect to one another and with respect to the vertebrae which define the intervertebral space. The plates may be removably attached to a base of the scaffold assembly or to the end plates of the vertebrae between which they are disposed. The surfaces of the plates which contact the disc prosthesis may be high friction surfaces, in which case the prosthesis is held more or less rigidly between the plates. Alternatively, the surfaces of the plates which contact the disc prosthesis may be low friction surfaces, in which case the disc prosthesis may have some limited lateral range of motion between the plates. The plates are desirably easily removable such that they may be easily replaced with plates of different dimensions to accommodate disc prostheses having a variety of shapes and sizes.

In embodiments where a disc prosthesis is removably contained within a restricted space defined by a scaffold assembly, the dimensions of the space should be designed to house the disc prosthesis snugly enough to stabilize the disc prosthesis in the intervertebral space.

The disc prosthesis may be of any suitable design provided it is able, together with the scaffold assembly, to simulate spinal motion and further provided it is adapted to be removably received by the scaffold assembly. In one desirable embodiment, the disc prosthesis is made up of a rotating joint composed of two complementary surfaces. In one design, the first surface is a convex surface, the second surface is a concave surface and the two surfaces fit together to form a ball-in-socket type joint.

Another aspect of the invention provides a method for revising a stabilizing element using the artificial disc prosthesis system. In this method, a first stabilizing element which is removably retained in an intervertebral space by a scaffold assembly is replaced by a second stabilizing element without removing the scaffold assembly. The "second stabilizing element" may be different from the first stabilizing element or may simply be the first stabilizing element to which repairs or alterations have been made. The method may involve the replacement of a disc prosthesis with a fusion prosthesis or vice versa. Alternatively, the method may entail the replacement of a first fusion prosthesis with a second fusion prosthesis. In another variation, the method may entail the replacement of a first disc prosthesis with a second disc prosthesis.

Yet another aspect of the invention provides a disc prosthesis that may be used in an artificial disc prosthesis system of the type described above. The artificial disc may be designed to provide a degree of shock absorption and flexibility similar to that of a natural disc. In one such design, the disc prosthesis includes a rotating joint composed of two articulating surfaces, one of which is a load bearing surface. The load bearing surface may be mounted on a flexible support on a base in a stressed manner allowing it to function in a spring-like fashion. The support may take on a variety of forms provided it allows the disc prosthesis to undergo a degree of compression and re-expansion when pressure is applied to the prosthesis. For example the support may be composed of one or flexible legs extending from the load bearing surface to the base.

In one embodiment, the disc prosthesis has a nested configuration. In a nested disc prosthesis, the disc prosthesis includes a rotating joint made from two complimentary surfaces, each mounted to one of a pair of reciprocally positioned internal bases or cups. Each of the internal bases or cups is mounted to one of a pair of larger external bases or cups that form an external reciprocal pair. The internal cups may be centered within their respective external cup or they may be offset with respect to the centers of the external cups in order to provide flexibility in the location of the axis-of-motion.

Further objects, features and advantages of the invention will be apparent from the following detailed description when taken in conjunction with the accompanying drawings.

DETAILED DESCRIPTION OF THE INVENTION

Figure 1:
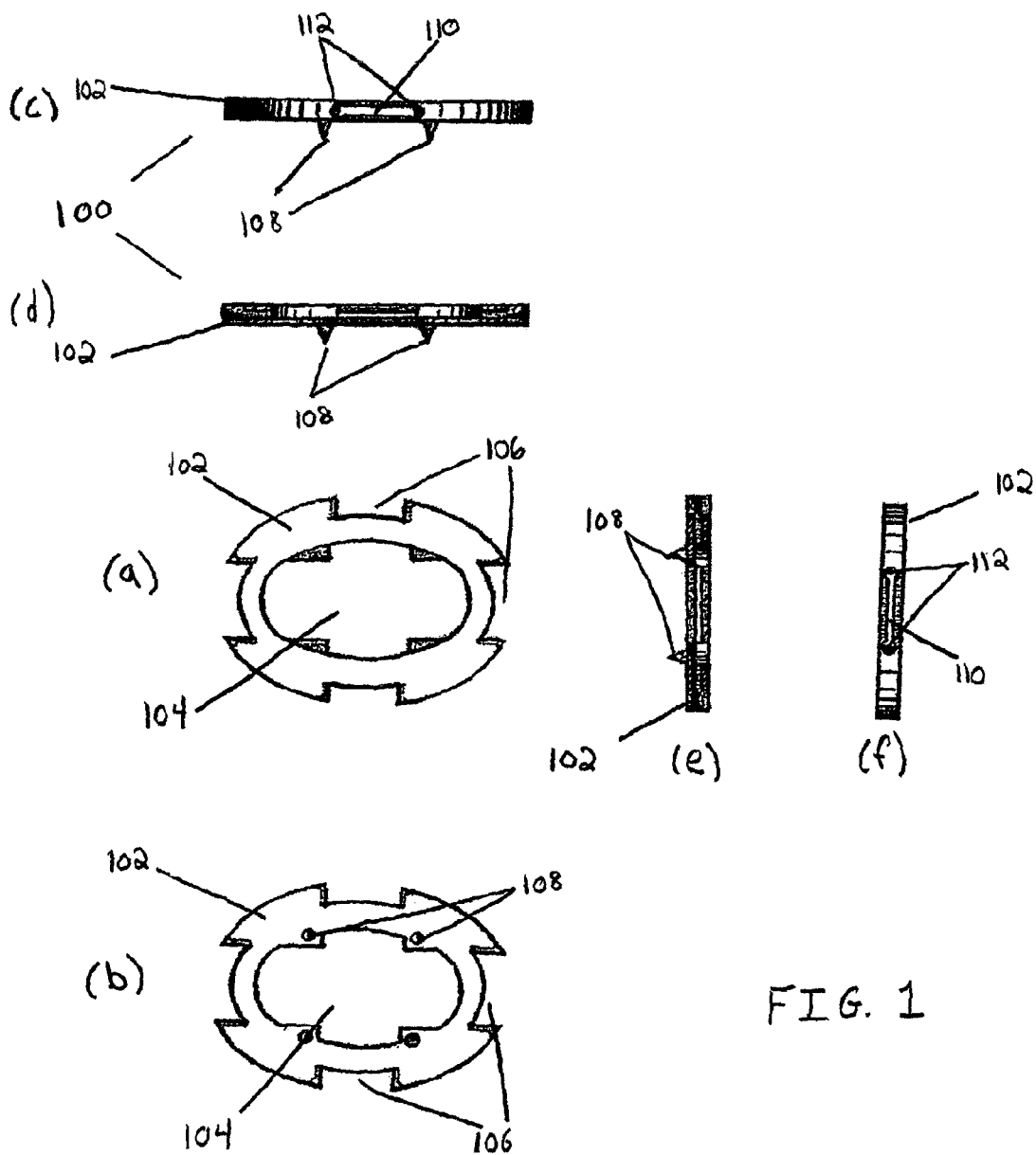
FIG. 1 shows an exemplary scaffold base for use in an artificial disc prosthesis system in accordance with the present invention.

The present invention relates to an artificial disc prosthesis system, a method for revising a stabilizing element using the artificial disc prosthesis system, and a disc prosthesis that may be used in the artificial disc prosthesis system. The artificial disc prosthesis system includes a scaffold assembly adapted to removably receive a stabilizing element, such as a disc prosthesis or a fusion prosthesis and a stabilizing element removably retained by the scaffold assembly. The scaffold assembly may be adjusted to accommodate stabilizing elements having different sizes and shapes. Stabilizing elements may include any element that stabilizes two adjacent vertebrae in a spinal column in the absence of a vertebral disc. Common examples of stabilizing elements include disc prostheses and fusion prosthesis. The disc prosthesis may be of any of a wide variety of known and commercially available disc prostheses designed to simulate spinal motion.

By providing an adjustable scaffold assembly and a removable stabilizing element, the artificial disc prosthesis system makes it possible to replace, repair and/or upgrade an existing disc prosthesis or fusion prosthesis without having to remove and reinstall the entire system. Once the scaffold assembly has been installed, a surgeon can replace a disc prosthesis without having to disconnect the original disc prosthesis from, and without having to reattach the new disc prosthesis to, the vertebrae or vertebrae end plates between which the disc prosthesis sits. Instead the original disc prosthesis need only be removed from, and the new disc prosthesis need only be received by, the scaffold assembly. This reduces the trauma to the patient and helps prevent weakening of the vertebrae. In certain embodiments, the system further provides the ability to replace the disc prosthesis with a fusion prosthesis without removal of the entire scaffold assembly.

For the purposes of this disclosure a disc prosthesis which is "removably received" or "removably retained" by a scaffold assembly is one that is held within an intervertebral space without any direct attachments between the disc prosthesis itself and the vertebrae or vertebral end plates that define the intervertebral space. Thus, a disc prosthesis which is "removably received" or "removably retained" by a scaffold assembly may be removed from the intervertebral space without the need to break any direct attachments between the disc prosthesis and the vertebrae or vertebral end plates that define the intervertebral space. Instead the disc prosthesis may be removed simply by disconnecting and/or removing the disc prosthesis from the scaffold assembly. The scaffold assembly may be designed to allow for the removal of the disc prosthesis via an anterior, anterolateral, or lateral approach.

The scaffold assembly may take on a wide variety of shapes and sizes provided it is adapted to removably receive a disc prosthesis. As such, the geometry of the scaffold assembly will be dictated, at least in part, by the disc prosthesis to be employed. The scaffold assembly may be composed of a single unit attached to a single vertebra. Alternatively, the scaffold assembly may be composed of two separate units, each attached to a different vertebrae, which together form the assembly. In the latter embodiment, an inferior scaffold unit may be attached to the end plate of an inferior vertebrae and a superior scaffold unit may be attached to the end plate of a superior vertebrae. While each scaffold unit may cover substantially the entire end plate, in one desirable embodiment the scaffold units leave a sufficient portion of the central area of the end plates exposed to allow for the insertion and fusion of a fusion prosthesis without the necessity for removing the entire scaffold assembly. Alternatively, the scaffold units can be designed to cover only a central portion of the inferior and superior end plates, such that at least a portion of the periphery of the end plates remain exposed. In this design an appropriate fusion prosthesis could be inserted into the intervertebral space around or over the scaffold assembly and fused into place without removing the entire scaffold assembly.

The scaffold assembly may be made of any suitable biocompatible material known to be safe for spinal disc prostheses. Many such materials are well known. These include, but are not limited to, cobalt chrome, titanium, plastics, ceramics, such as zirconium oxide ceramic and aluminum oxide ceramic, and other composites. The scaffold assembly may optionally have a coating to assist with bony ingrowth. This scaffold assembly may be anchored to the superior and inferior end plates via any suitable means, such as but not limited to pegs, spikes, screws and the like.

The scaffold assembly includes at least one base which is attached to the end plate of one the vertebra that define the intervertebral space. The base may include one or more fixation points to which a disc prosthesis may be directly, but removably attached. For example the fixation points may include screw holes, pin holes, clamps, snaps, hooks or similar means for attaching the disc prosthesis to the base. Appendages, such as buttresses and plates, may also be removably attached to the base. The appendages may themselves include fixation points. As described in greater detail below, these appendages may be used to define a space into which a disc prosthesis may be inserted. In addition, the removable buttresses may serve as extension or lateral bending or flexion constraints. These buttresses may have variable sizing to vary the degree of constraint in one or more directions.

The disc prostheses for use with the scaffold assemblies provided herein include a wide range of disc prosthesis technologies. Many suitable disc prosthesis technologies are well known and commercially available. Suitable disc prosthesis technologies include, but are not limited to, mechanical, hydraulic, gas and liquid filled, elastomeric and functionally similar prosthetic discs. In some cases, the disc prostheses may be suitable as sold for use with the scaffold assemblies. In other cases, the disc prosthesis may require some modification in order to facilitate their attachment to the scaffold assembly. For example, attachment means, such as screws, pins, screw holes, pin holes, and the like may need to be added to the disc prosthesis. Examples of disc prostheses that may be used with the scaffold assemblies with no modification of only minor modification include those described in U.S. Pat. Nos. 5,314,477; 5,562,738; and 6,517,580.

In one embodiment, the disc prosthesis has two sections. The two sections are disposed opposite one another when the disc prosthesis is in place and each of the two sections includes a contoured surface that is complementary to the opposing surface. As used herein, complementary surfaces are surfaces that fit together in such a way as to provide a rotating joint. For example, one surface may be a concave surface and the opposing surface may be a convex surface. These surfaces may be disposed to fit together to form a ball-in-socket type joint. The first surface will typically be supported on a first base and the second surface will typically be supported on a second base. Desirably, one or both of the surfaces are mounted in the bases in a manner that provides some flexibility between the bases and the surfaces when pressure is applied to the disc prosthesis. This design allows the disc prosthesis to compress and expand between the vertebrae, behaving as a spring and a shock absorber.

In one embodiment the bases which support the complementary surfaces each include a floor and a wall, to form a cylindrical "cup." One cup may be larger than the other such that rim of the smaller cylindrical cup fits within the rim of the reciprocally positioned larger cup when the artificial disc prosthesis system is in place. Two cups may be considered reciprocally positioned if the cups are positioned across from each other in a substantially parallel relationship with the inner cup surfaces facing one another. In this design, the larger outer cup may serve to contain wear debris that might otherwise stimulate an inflammatory response as often seen in deteriorating, peripheral joint replacements. The relative size of these cups may vary to control the degree of global constraint. The cups are desirably metallic with high friction outer surfaces. The high friction surfaces allow the disc prosthesis to rest securely within the constraints of a scaffold assembly. Alternatively, cups may be provided with low friction outer surfaces that allow them to rest within the constraints of a scaffold assembly with some limited ability to move.

The larger outer cup may include a convex internal surface that is capable of articulating with a load bearing, force absorbing, complimentary surface disposed within in the smaller cup. This load bearing surface has a concave surface to complement the opposing internal surface. In some embodiments, this relationship may be reversed. The load bearing surface may be metallic and may be mounted on a flexible support inside the smaller cup in a stressed manner allowing it to function in a spring-like fashion. The support may take on a variety of forms provided it allows the disc prosthesis to undergo a degree of compression and re-expansion when pressure is applied to the prosthesis. For example the support may be composed of two or more flexible legs extending radially outwardly from the load bearing surface to the base. Alternatively, the support may be composed of a single leg wrapped around and extending from the circumference of the disc prosthesis to the base. In this configuration the leg may take the shape of a truncated cone extending from the disc prosthesis to the base. The cone may provide flexibility by bulging or bending outwardly or inwardly when pressure is applied to the prosthesis. In one embodiment the shape of this support is cruciatek (e.g. composed of four equi-spaced flexible legs), but other shapes may be used. The support may also be elastomeric, or hydrogel resting snugly inside the smaller cup.

A nested disc prosthesis design also may be used, providing flexibility, in the axis-of-motion location. In this design, the disc prosthesis includes a rotating joint composed of two complimentary surfaces, each mounted to one of a pair of reciprocal internal bases or cups. Each of the internal bases or cups is itself mounted to one of a pair of larger external bases or cups that form an external reciprocal pair. The nested disc prosthesis may be removably retained by a scaffold assembly to form an artificial disc prosthesis system. The nested disc prosthesis design is advantageous because the central axis of the reciprocal internal bases or cups need not coincide with the central axis of the larger cups, thus allowing for compensation of any difficulties with or misalignment of the scaffold assembly and for proper location of the axis-of-motion.

Exemplary embodiments of an artificial disc prosthesis system and disc prostheses for use therein will now be explained with reference to the figures. This description is provided in order to assist in the understanding of the invention and is not intended to limit the scope of the invention to the embodiments shown in the figures or described below.

FIGS. 1a through 1f show different views of an exemplary scaffold assembly for use in an artificial disc prosthesis system in accordance with the present invention. FIG. 1a shows a top view of a scaffold base 100 composes of a ring 102 which defines a central opening 104. Buttress ports 106 are provided along the outer periphery of the ring for attaching buttresses (not shown) to the base 100. FIG. 1b shows a bottom view of the base 100. As shown in the figure, the bottom surface of the ring 102 includes a number of fixation pegs 108 which may be used to rigidly attach the base to the end plate of a vertebra. FIGS. 1c and 1f show the front and side views of the base and FIGS. 1d and 1e show cross-sectional front and side views of the base. As best shown in FIGS. 1c and 1f, the buttress ports 106 include slots 110 into which an insert tab on a buttress (not shown) may be inserted in order to align the buttress with the base. The slot edges 112 on either end of the slot may be tapped.

Figure 2:
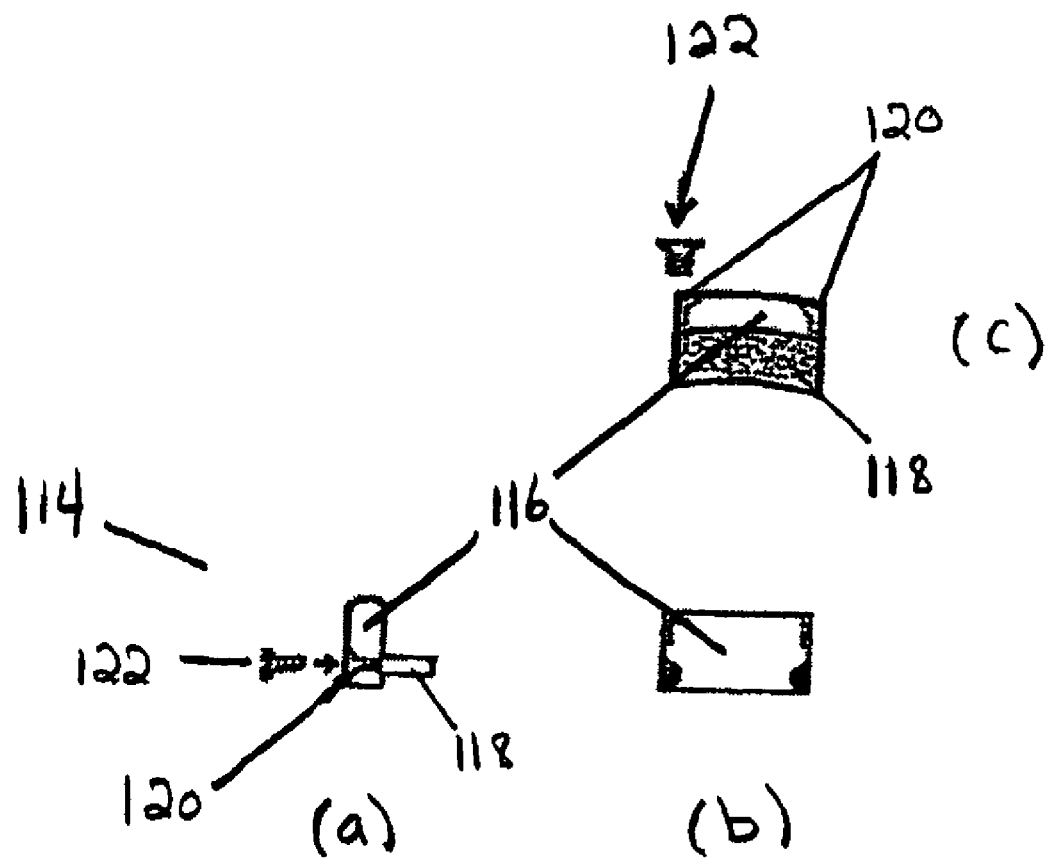
FIG. 2 shows a buttress that may be connected to a base of a scaffold assembly in accordance with the present invention.

FIGS. 2a through 2c show a side, front, and cross-sectional bottom view, respectively, of a buttress 114 that may be connected to a scaffold base, such as that shown in FIGS. 1a through 1f. The buttress has a bumper 116 which extends from the base 100 toward the center of the intervertebral space when the buttress is in place. The buttress also includes an insert tab 118 which fits into a slot 110 in a buttress port 106 on the base of the scaffold 100. The buttress may be attached to the base in any suitable manner that allows the buttress to the removed or realigned after the scaffold assembly is implanted into the body. For example, as shown in the figures, the buttress may have tapped grooves 120 along the edge of and extending into its front face. When the buttress 114 is in place along the periphery of the base 100, the tapped grooves 120 together with the tapped slot edges 112 form screw holes into which a screw 122 may be inserted to removably attach the buttress to the scaffold base 100.

Figure 3:
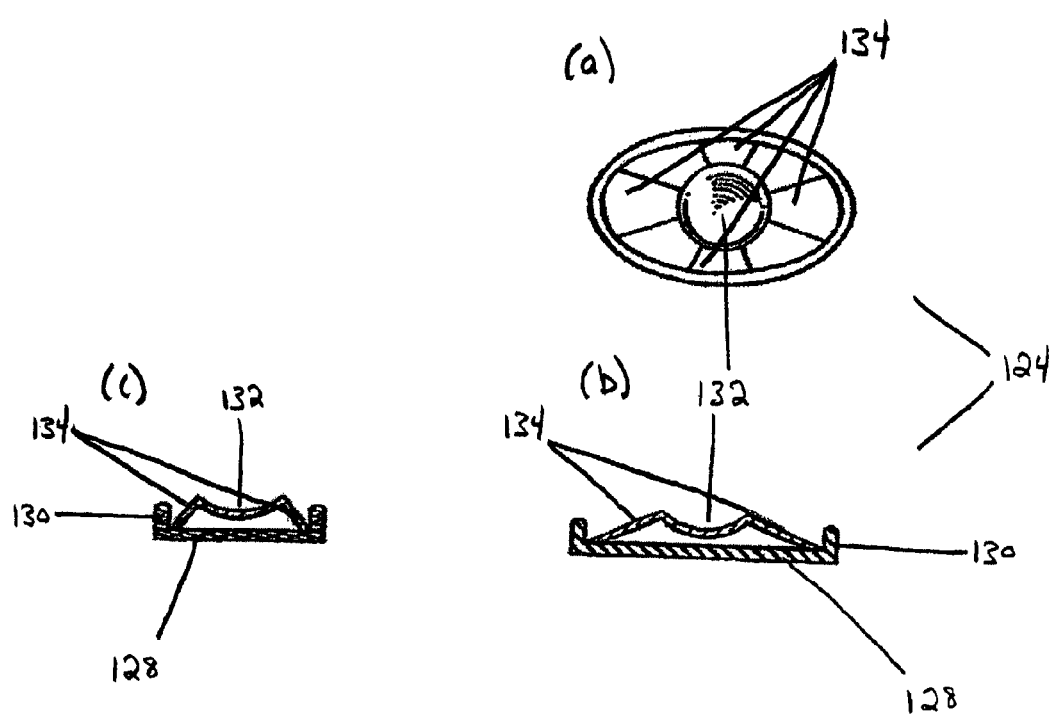
FIG. 3 shows the first part of a two-part disc prosthesis that may be used with an artificial disc prosthesis system in accordance with the present invention.
Figure 4:
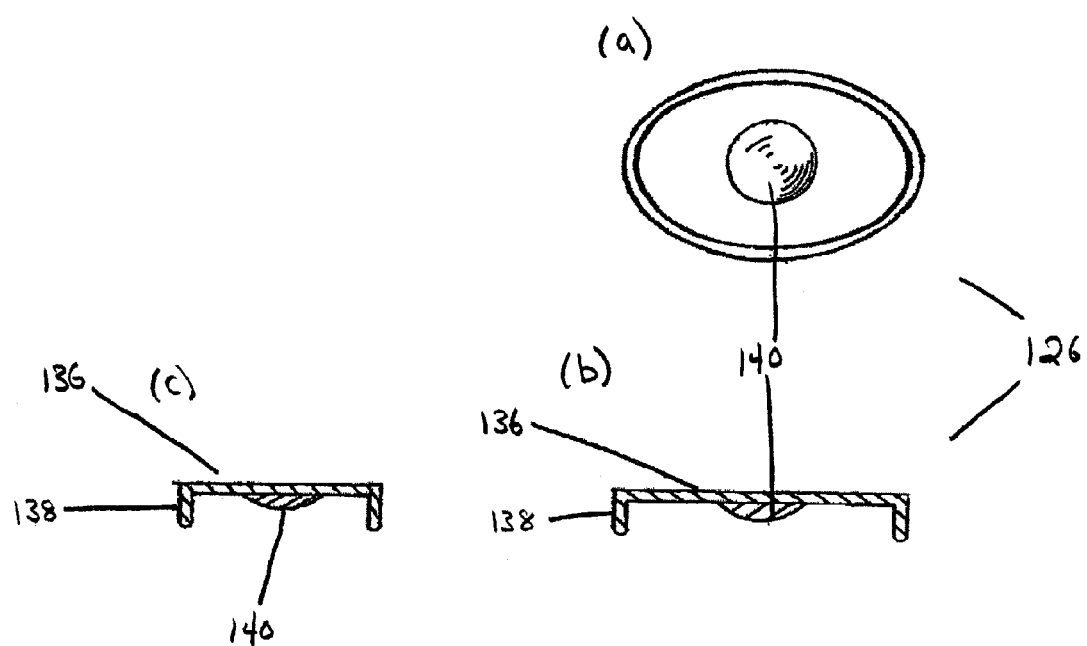
FIG. 4 shows the second part of a two-part disc prosthesis that may be used with an artificial disc prosthesis system in accordance with the present invention.

FIGS. 3 and 4 depict a disc prosthesis that may be used with an artificial disc prosthesis system in accordance with the present invention. The disc prosthesis includes two sections 124 and 126. FIGS. 3a through 3c show top, cross-sectional front and cross-sectional side views, respectively, of the first section 124. The first section includes a base, having a floor 128 and an outer wall 130, and a concave surface 132 which is supported by a number of legs 134 which extend outwardly and downwardly from the concave surface 132 to the floor 128 of the base. The legs 134 desirably flex in a spring-like fashion. FIGS. 4a through 4c show top, cross-sectional front and cross-sectional side views, respectively, of the second section 126 of the disc prosthesis. The second section includes a base, having a floor 136 and an outer wall 138, and a convex surface 140 extending outwardly from the floor 136 of the base. The concave surface 132 is complementary to and capable of articulating with the convex surface 140 to form a rotating joint. The outer wall 130 of the first section 124 may have a smaller diameter than the outer wall 138 of the second section 126, or vice versa, such that the smaller section fits into the larger section in a nested configuration when the disc prosthesis is in place.

FIGS. 5a through 5c show a plate assembly 142 that may be used to removably retain a disc prosthesis, such as that shown in FIGS. 3 and 4, within a scaffold assembly. The plate assembly includes a plate 144 and a fixation mount 146. The fixation mount 146 may be disposed through the central opening 104 of the base of the scaffold 100 and a screw (not shown) or other attachment means may be inserted through the fixation mount to attach the plate assembly directly to a vertebra end plate.

Figure 5:
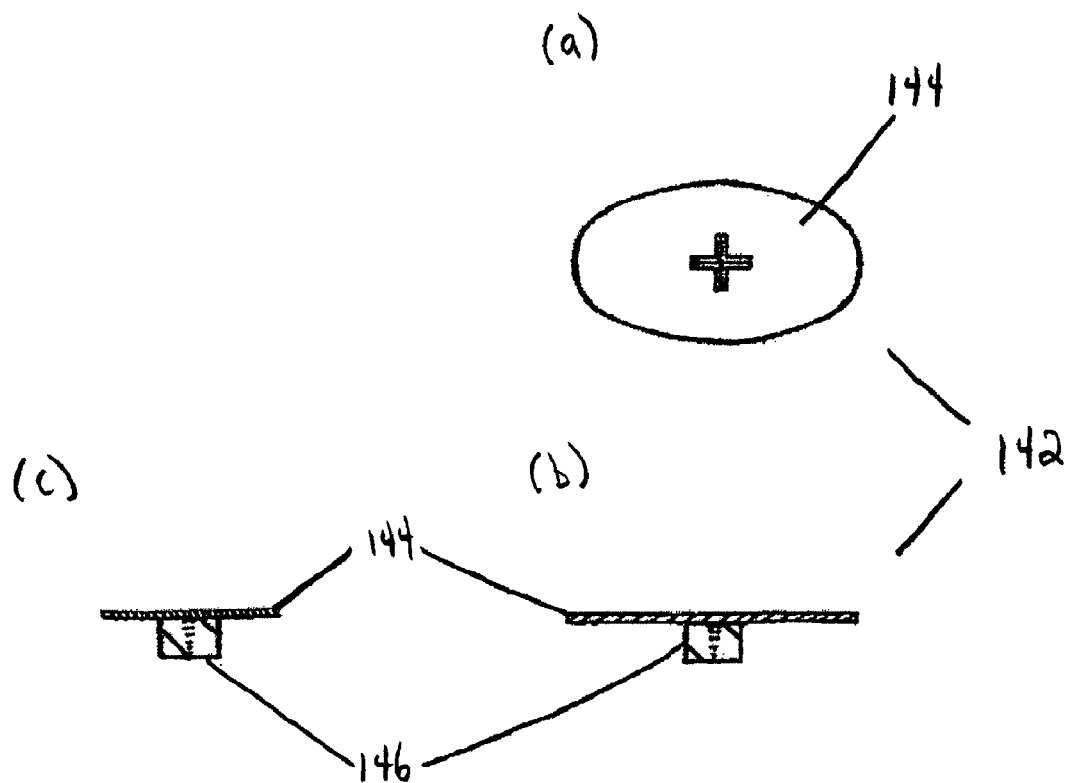
FIG. 5 shows a plate assembly for use in an artificial disc prosthesis system in accordance with the present invention.
Figure 6:
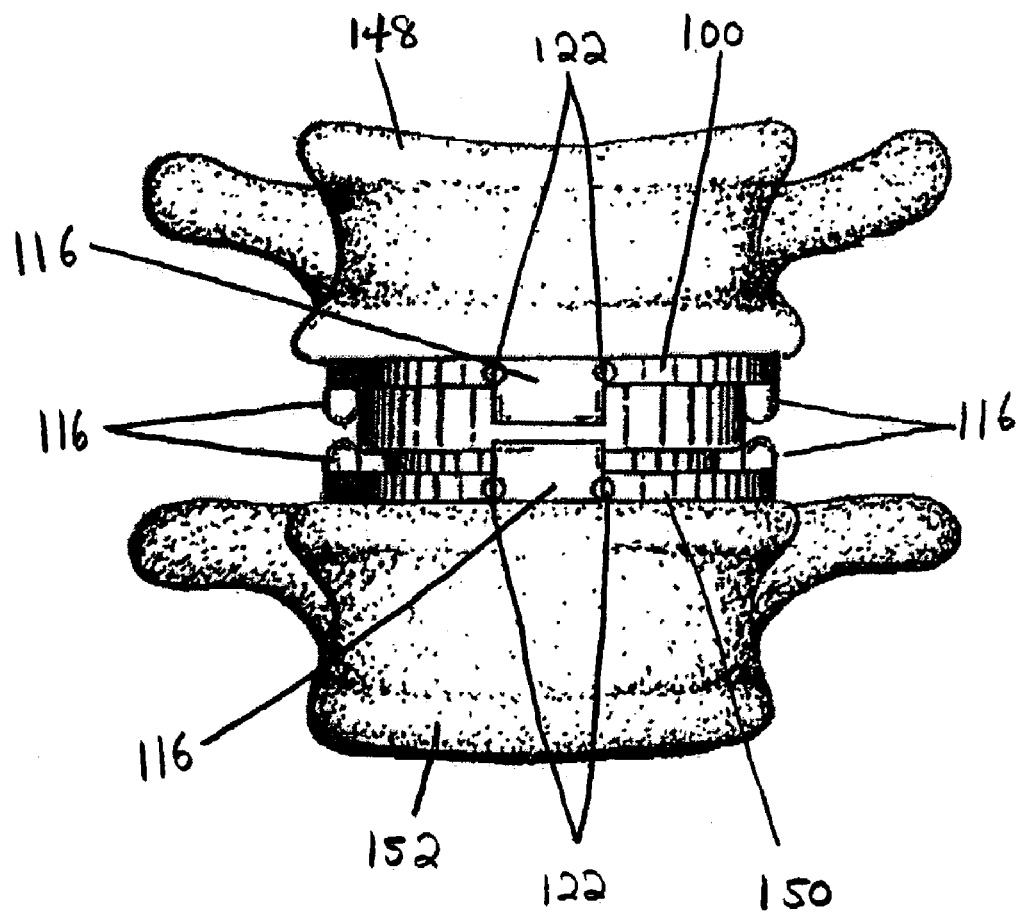
FIG. 6 shows a front view of an artificial disc prosthesis system disposed within an intervertebral space in accordance with the present invention.
Figure 7:
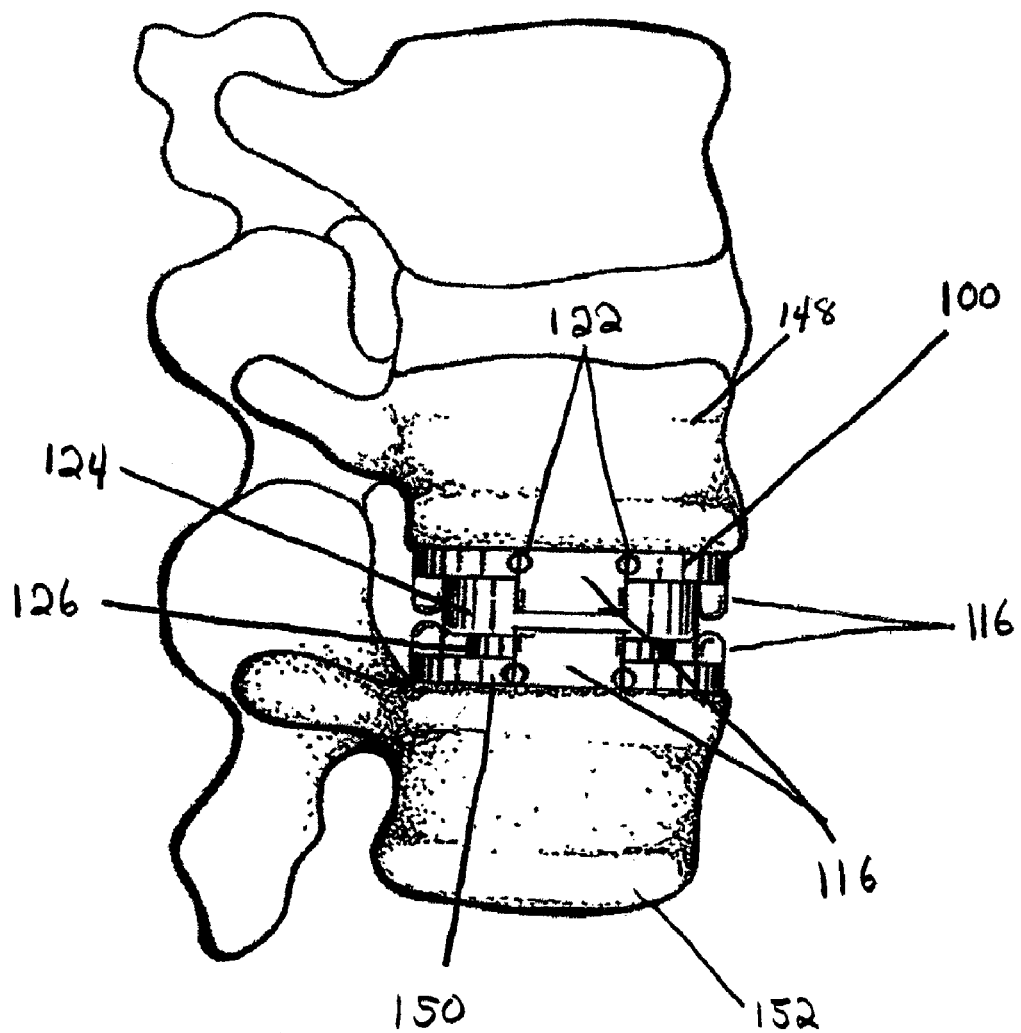
FIG. 7 shows a side view of an artificial disc prosthesis system disposed within an intervertebral space in accordance with the present invention.

FIGS. 6 and 7 show the front and side views of an exemplary artificial disc prosthesis system disposed within an intervertebral space, in accordance with the present invention. This system includes a scaffold assembly with a superior base 100 of the type shown in FIG. 1 attached to a superior vertebra 148 and an inferior base 150, also of the type shown in FIG. 1, attached to an inferior vertebra 152. A disc prosthesis of the type shown in FIGS. 3-5 is located between the scaffold bases and includes a first section 124 and a second section 126. The second section 124 has a smaller diameter than the first section 126 and fits within the first section 124 in a nested position. Buttresses, each having a bumper 116, are attached to the periphery of the bases 100 and 150 with screws 122. The bumpers 116 extend upwardly or downwardly beyond the bases 100 and 150 to form a cage in which the disc prosthesis is removably housed.

Figure 8:
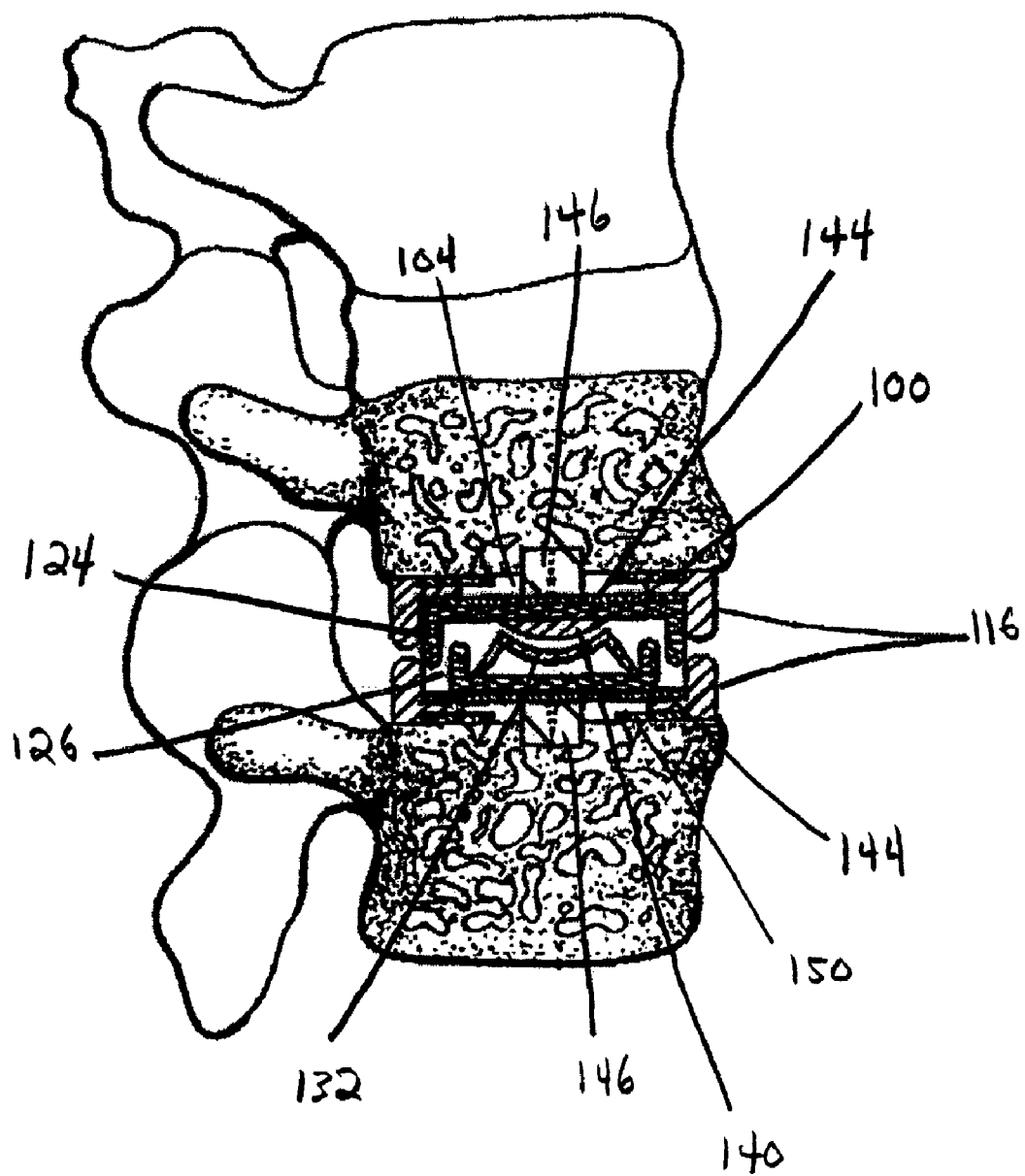
FIG. 8 shows a cross-sectional front view of an artificial disc prosthesis system disposed within an intervertebral space in accordance with the present invention.
Figure 9:
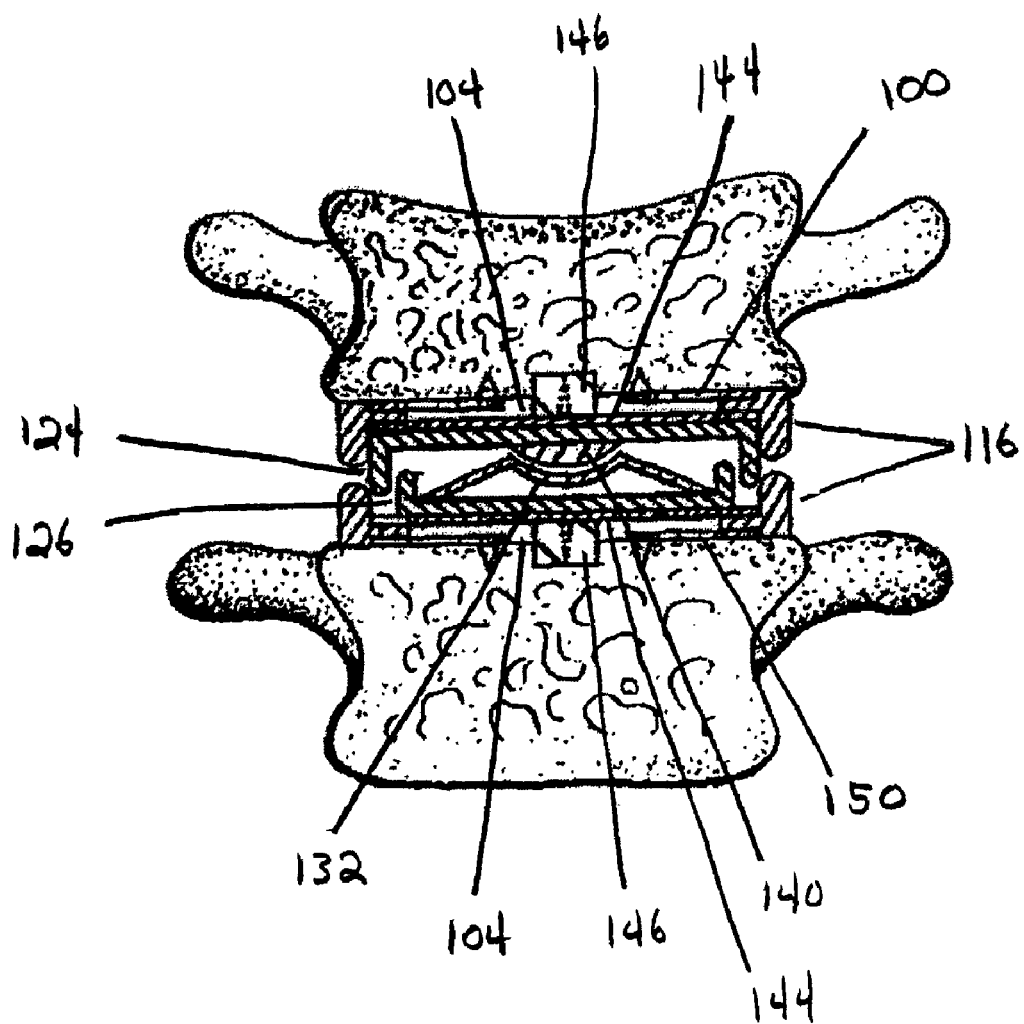
FIG. 9 shows a cross-sectional side view of an artificial disc prosthesis system disposed within an intervertebral space in accordance with the present invention.
Figure 10:
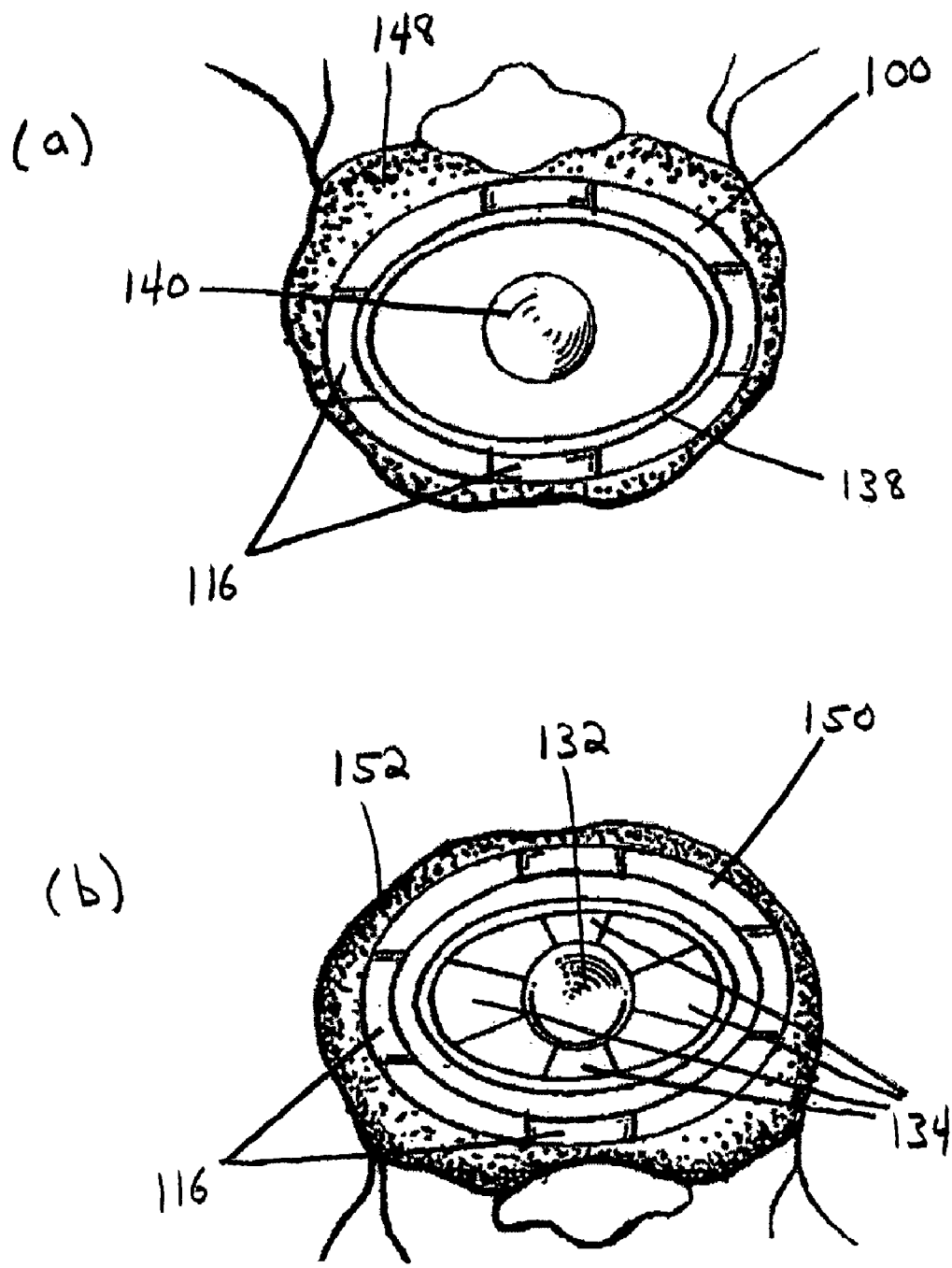
FIG. 10 shows a bottom view of the top part of an artificial disc prosthesis system disposed within an intervertebral space in accordance with the present invention and a top view of the bottom part of an artificial disc prosthesis system disposed within an intervertebral space in accordance with the present invention.
Figure 11:
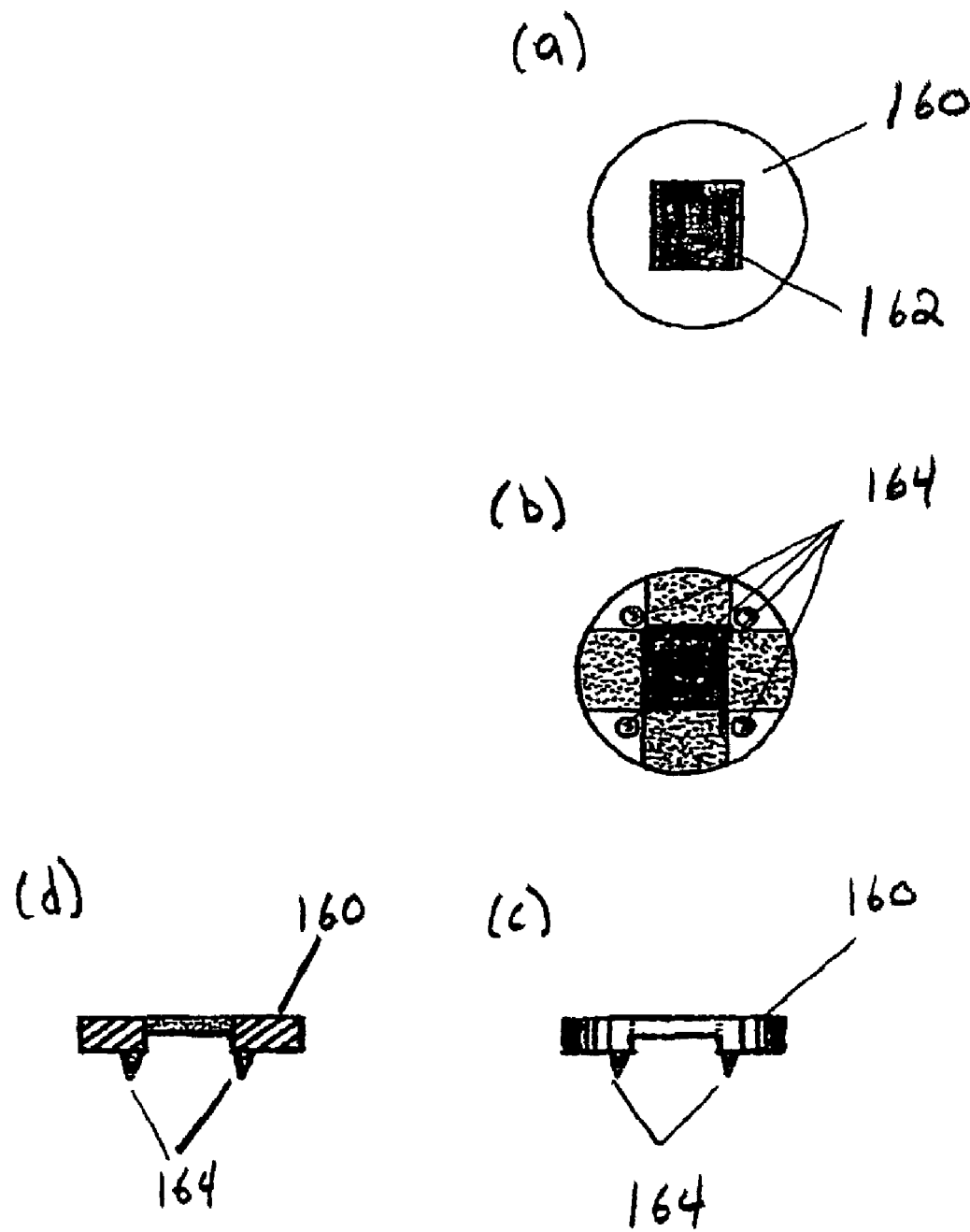
FIG. 11 shows an exemplary scaffold base for use in an artificial disc prosthesis system in accordance with the present invention.

FIGS. 8 and 9 show cross-sectional front and side views, respectively, of the artificial disc prosthesis system of FIGS. 6 and 7. The cross-sectional views show that the superior base 100 and the inferior base 150 define central openings 104 that leave the central portions of the end plates (not depicted) of the superior vertebra 148 and the inferior vertebra 152 uncovered. The superior scaffold base 100 and the inferior scaffold base 150 are rigidly attached to the superior vertebra 102 and the inferior vertebra with fixation pegs 108. FIG. 10a shows the view looking up at the top part of the artificial disc prosthesis system from the intervertebral space. FIG. 10b shows the view looking down on the bottom part of the artificial disc prosthesis system from the intervertebral space.

FIGS. 11a through 11d show bottom, top, front, and cross-sectional side views, respectively, of an exemplary scaffold base for use in an artificial disc prosthesis system in accordance with the present invention. The scaffold base depicted in these figures is designed to be attached to a central portion of the end plate of a vertebra, leaving the peripheral portions of the end plate exposed. The scaffold base is composed of a ring 160 that defines a central opening 162. The ring 160 may be attached to a vertebral end plate with a series of fixation pegs 164.

Figure 12:
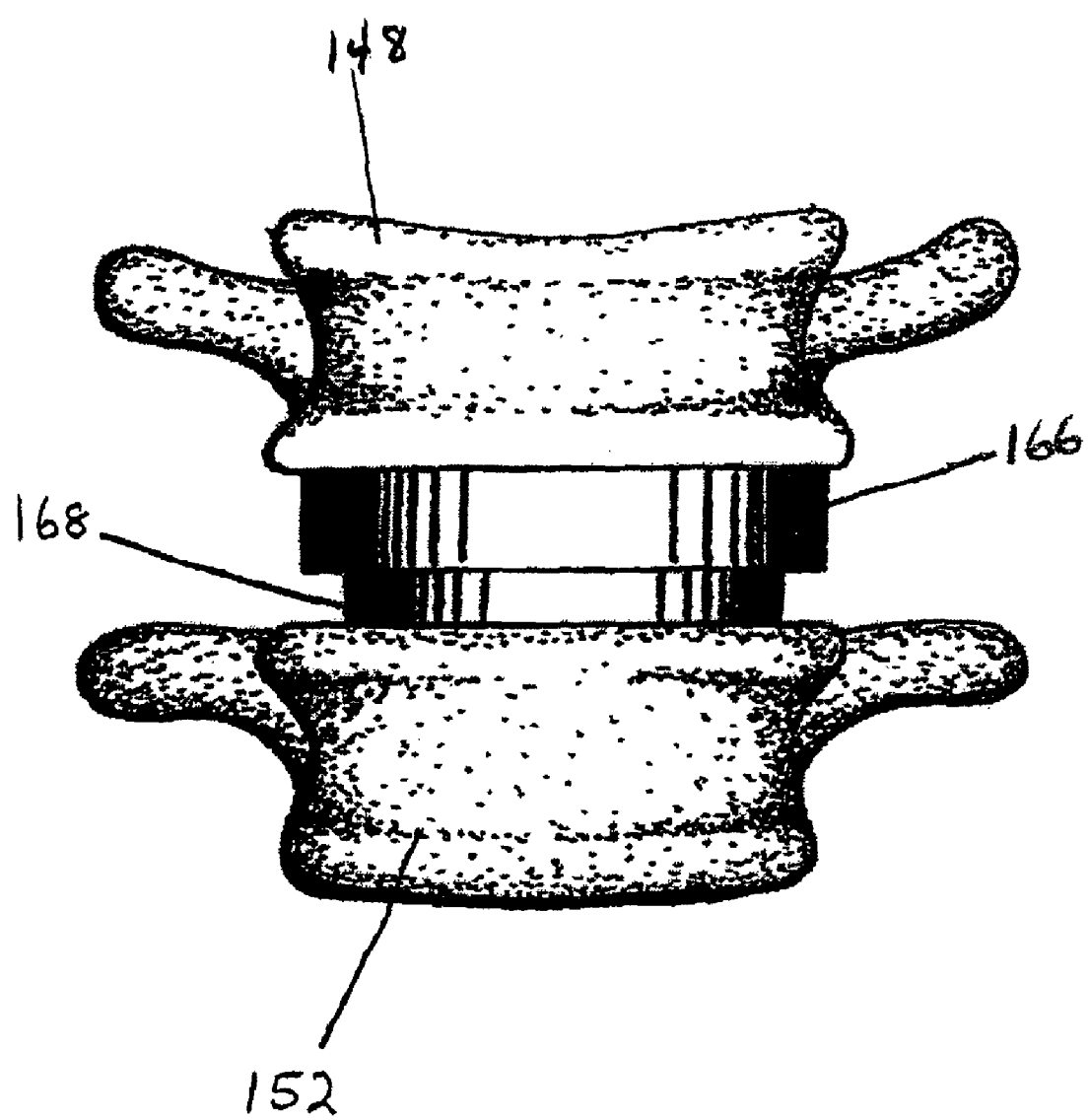
FIG. 12 shows a front view of an exemplary embodiment of an artificial disc prosthesis system disposed within an intervertebral space in accordance with the present invention.
Figure 13:
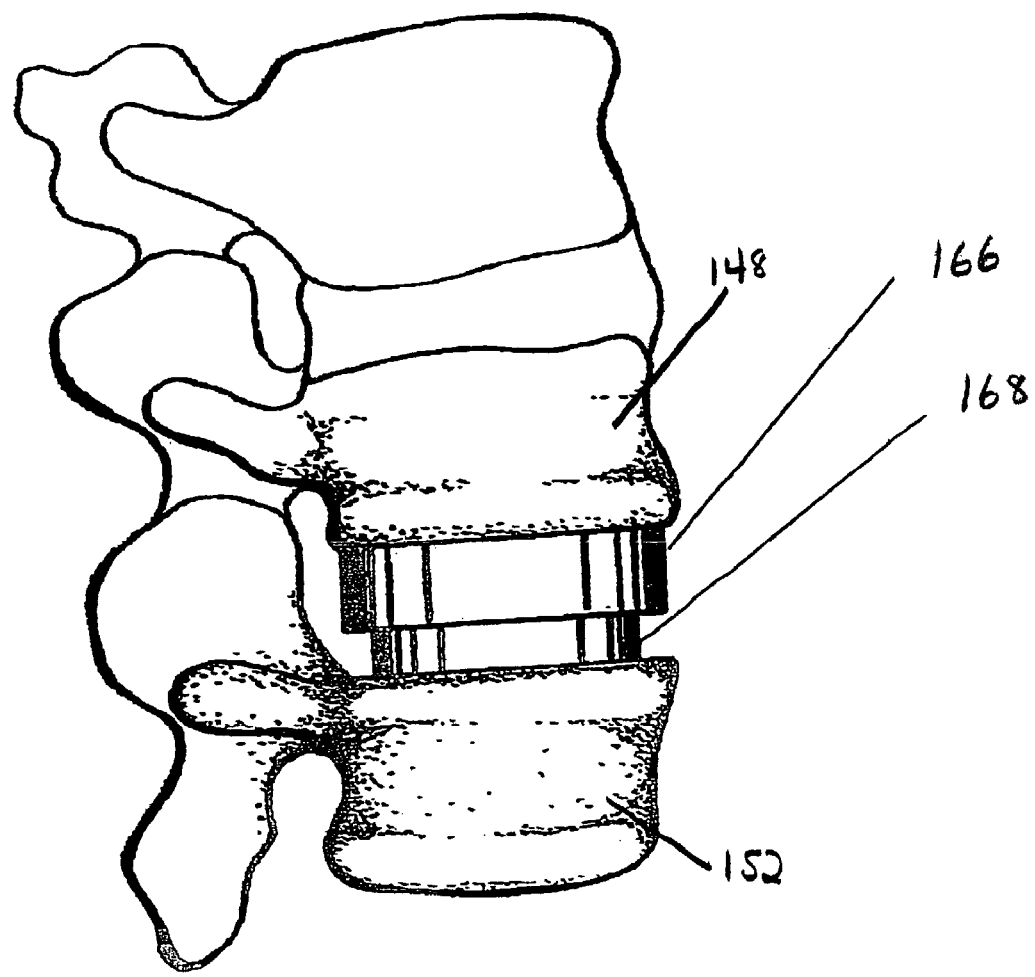
FIG. 13 shows a side view of an exemplary embodiment of an artificial disc prosthesis system disposed within an intervertebral space in accordance with the present invention.
Figure 14:
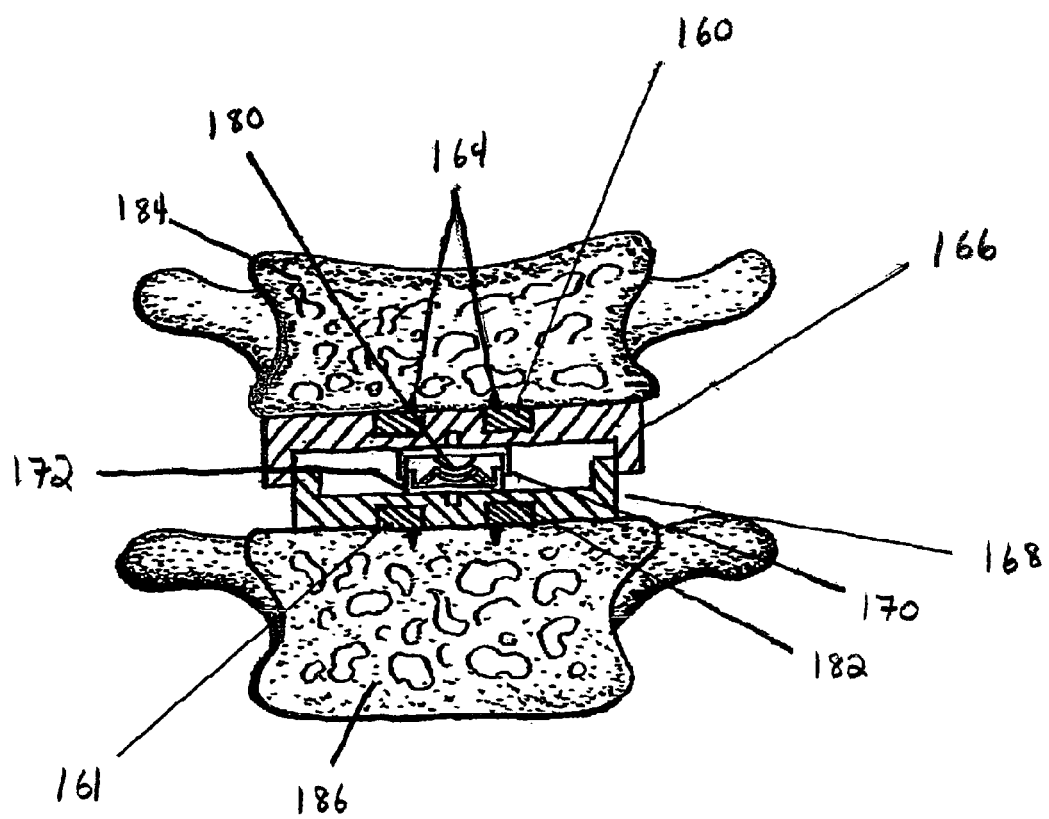
FIG. 14 shows a cross-sectional front view of an exemplary embodiment of an artificial disc prosthesis system disposed within an intervertebral space in accordance with the present invention.
Figure 15:
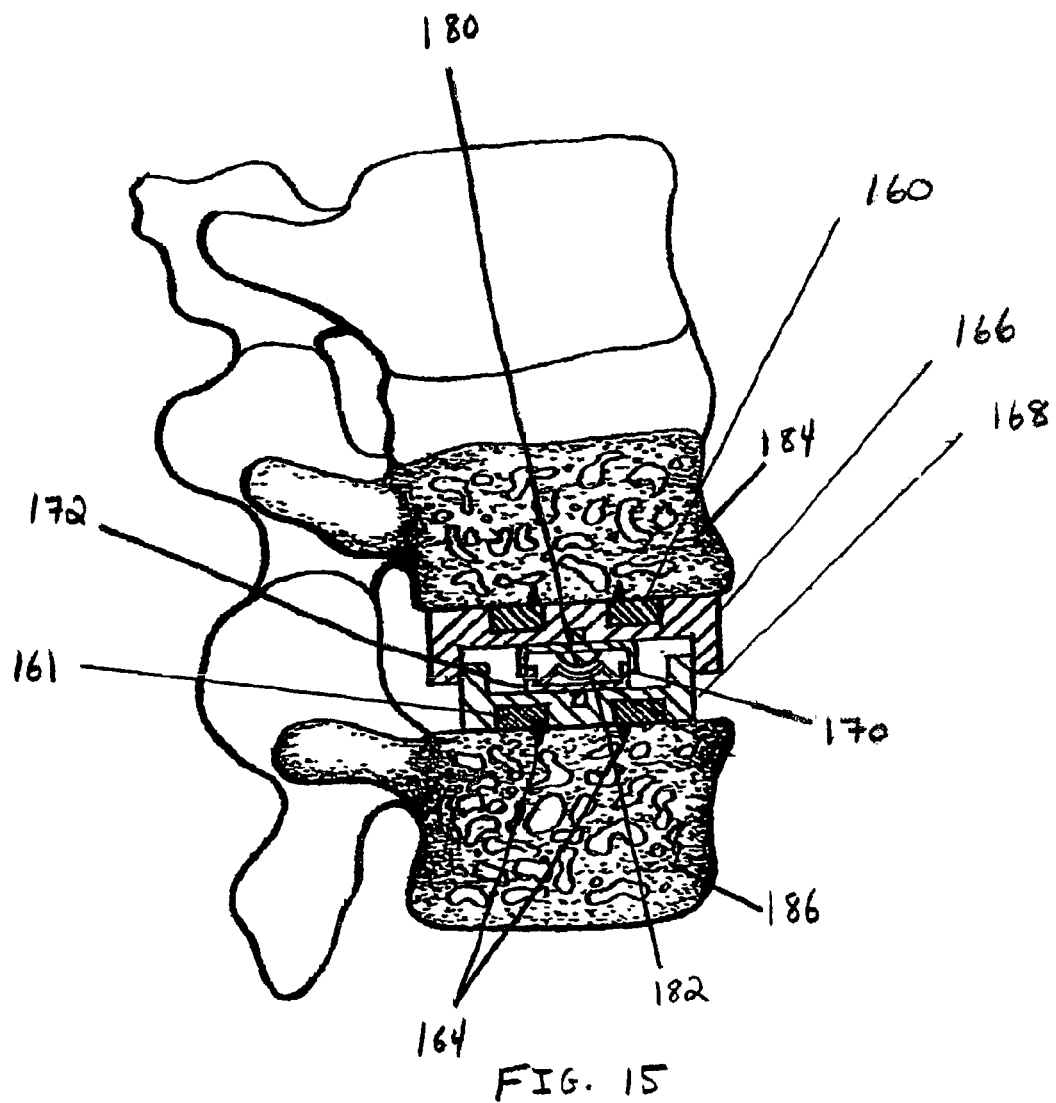
FIG. 15 shows a cross-sectional side view of an exemplary embodiment of an artificial disc prosthesis system disposed within an intervertebral space in accordance with the present invention.

FIGS. 12 and 13 show the front and side views of an exemplary artificial disc prosthesis system disposed within an intervertebral space. FIGS. 14 and 15 show cross-sectional front and side views of the artificial disc prosthesis system depicted in FIGS. 12 and 13. The disc prosthesis, which is best shown in FIGS. 14 and 15, has a "nested disc prosthesis" configuration. The disc prosthesis includes a convex surface 180 mounted in a superior internal cup 170 and a complementary concave surface 182 mounted in a reciprocal inferior internal cup 172. The superior internal cup 170 is attached to a superior external cup 166 and the inferior internal cup 172 is attached to an inferior external cup 168. The superior external cup 166 is removably retained by a superior scaffold base 160 and the inferior external cup 168 is removably retained by an inferior scaffold base 161. The superior and inferior scaffold bases are attached to a superior vertebra 184 and an inferior vertebra 186. The internal cups may be attached to the external cups using any suitable means including, pins, pegs, screws and the like at suitable fixation points 188 (e.g. screw holes, pin holes, snaps, hooks, and the like) on the external cups. Similarly, the external cups may be removably attached to the scaffold bases using any suitable means. In one embodiment the external cups are snapped onto the scaffold bases.

Figure 16:
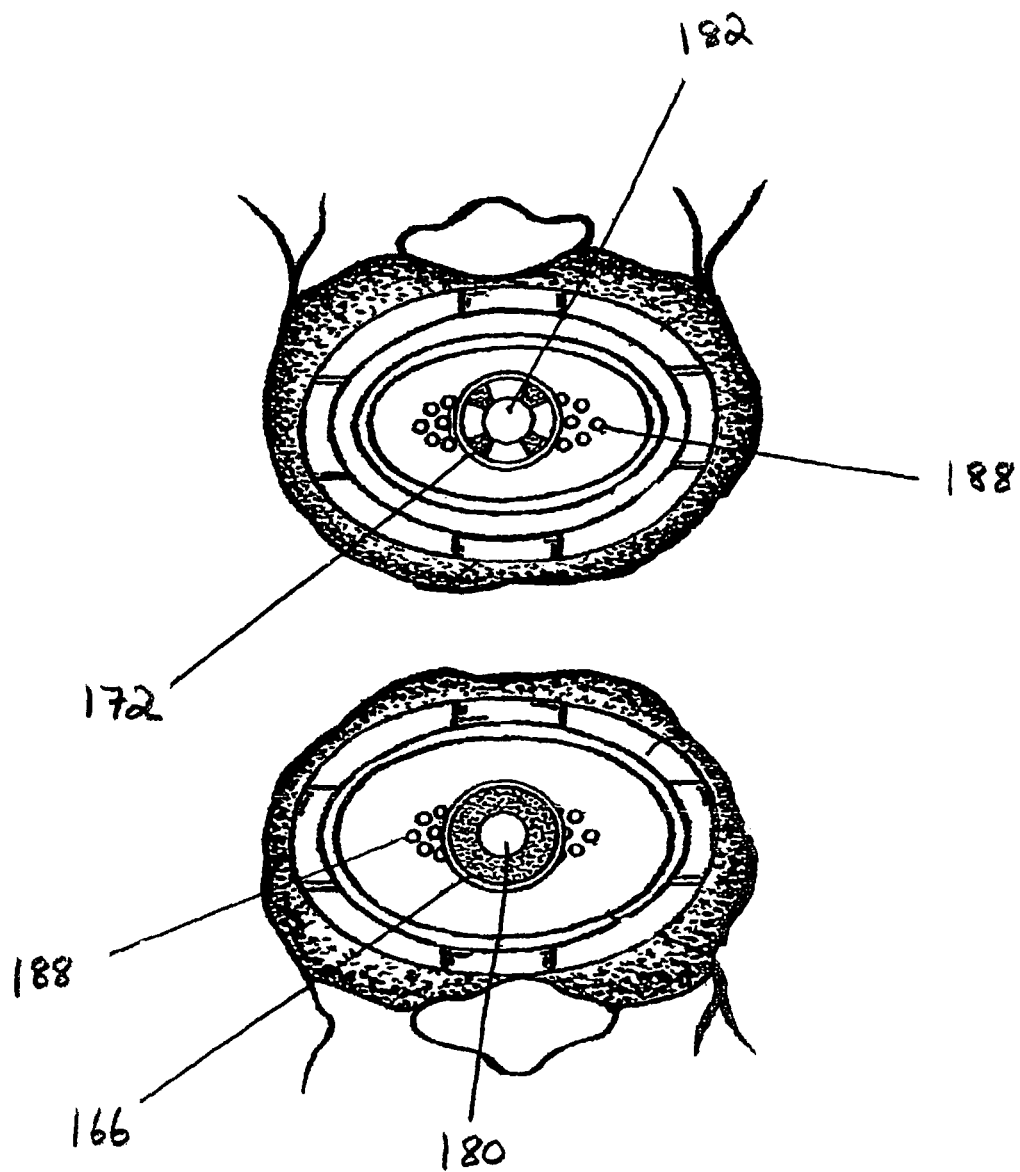
FIG. 16 shows a bottom view of the top part of an artificial disc prosthesis system disposed within an intervertebral space in accordance with the present invention and a top view of the bottom part of an artificial disc prosthesis system disposed within an intervertebral space in accordance with the present invention.
Figure 17:
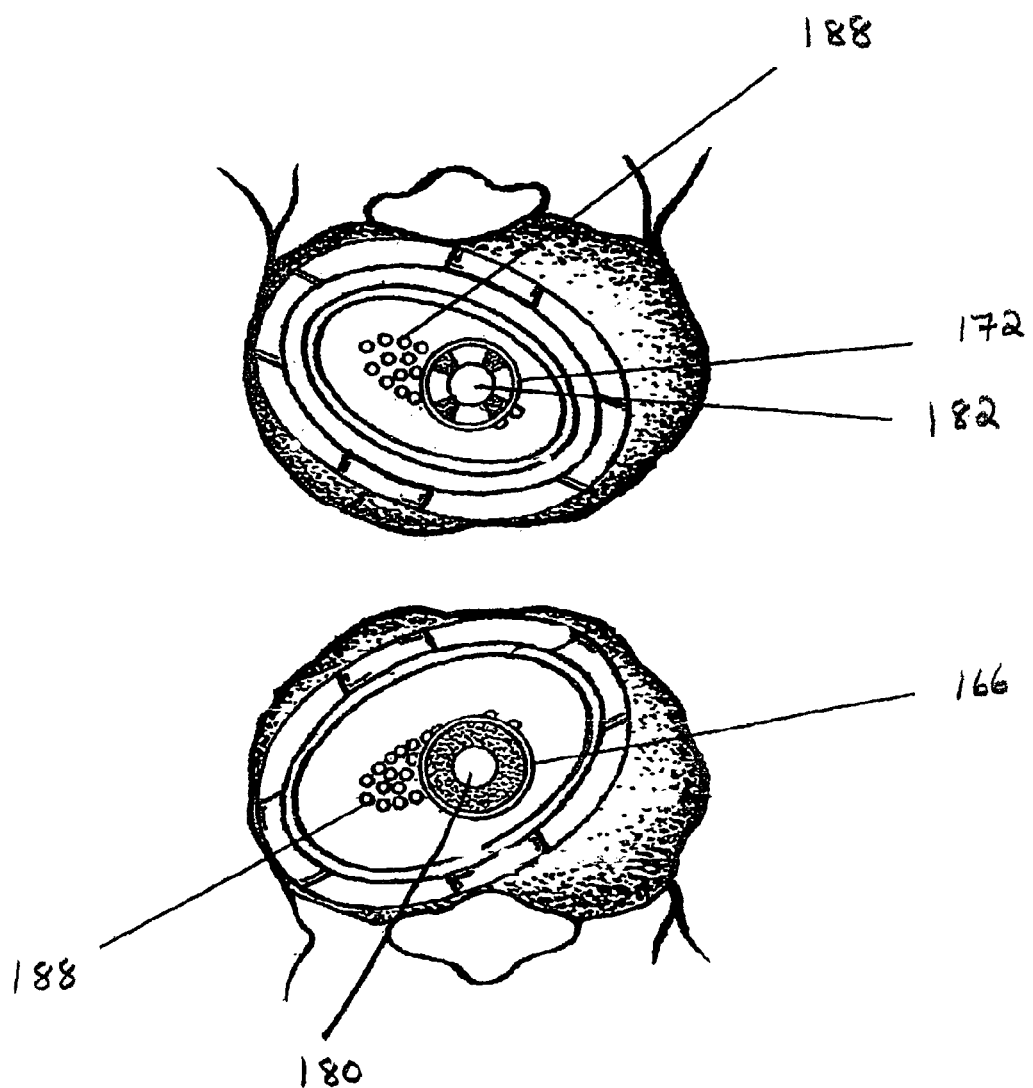
FIG. 17 shows an artificial disc prosthesis system wherein the central disc prosthesis is mounted in an offset position.

FIG. 16a shows the view looking up at the top part of the artificial disc prosthesis system of FIGS. 12-15 from within the intervertebral space. FIG. 16b shows the view looking down at the bottom part of the artificial disc prosthesis system of FIGS. 12-15 from within the intervertebral space. In this figure the interior cups 170 and 172 are substantially centered within the external cups 166 and 168. However, as shown in FIGS. 17a and 17b, the internal cups may also be mounted in an offset location within the external cups.

It should be understood that various changes and modifications to the embodiments described herein would be apparent to those skilled in the art. Such changes and modifications can be made without departing from the spirit and scope of the present invention and without demising its attendant advantages. It is therefore intended that such changes and modifications be covered by the appended claims.

What is claimed is:

1. A disc prosthesis comprising:
   (a) a concave surface attached to a first base;
   (b) a convex surface attached to a second base; and
   (c) a ring-shaped scaffold base having a peripheral portion that defines an opening entirely through the scaffold base;
   wherein the concave surface and the convex surface together form a rotating joint and further wherein at least one of the concave and convex surfaces is attached to its base through at least one flexible support capable of flexing to provide shock absorption when the artificial disc prosthesis is disposed between two vertebra.

2. The disc prosthesis of claim 1, wherein the concave surface is attached to the first base through at least one flexible support.

3. The disc prosthesis of claim 1, wherein the convex surface is attached to the second base through at least one flexible support.

4. A disc prosthesis comprising:
   (a) a first external cup;
   (b) a first internal cup comprising a first inner surface, the first internal cup mounted to the inside of the first external cup;
   (c) a second external cup; and
   (d) a second internal cup comprising a second inner surface complementary to the first inner surface, the second internal cup mounted to the inside of the second external cup;
   wherein the first and second internal cups are disposed opposite one another such that the first and second inner surfaces contact one another to foam a rotating joint; and
   wherein one of the internal cups has a smaller diameter than the other internal cup such that the smaller internal cup fits at least partially within the larger internal cup when the first and second inner surfaces are in contact.

5. The disc prosthesis of claim 4, wherein the first internal cup is centered within the first external cup and the second internal cup is centered within the second external cup.

6. The disc prosthesis of claim 4, wherein the first internal cup is offset from the center of the first external cup and the second internal cup is offset from the center of the second external cup.

7. The disc prosthesis of claim 4, wherein one of the external cups has a smaller diameter than the other external cup such that the smaller external cup fits at least partially within the larger external cup when the first and second inner surfaces are in contact.

8. The disc prosthesis of claim 4, wherein the first inner surface is mounted on at least one flexible support capable of flexing to provide shock absorption.

9. A disc prosthesis comprising:
   (a) a first base comprising a floor and an outer wall;
   (b) a second base comprising a floor and an outer wall;
   (c) a concave surface supported on the floor of the first base;
   (d) a convex surface supported on the floor of the second base; and
   (e) a ring-shaped scaffold base having a peripheral portion that defines an opening entirely through the scaffold base;
   wherein the concave surface and the convex surface together form a joint and further wherein at least one of the concave and convex surfaces is supported by at least one flexible support capable of flexing to provide shock absorption when the artificial disc prosthesis is disposed between two vertebra.

* * * * *